(12) United States Patent
Maehara (10) Patent No.: US 11,466,120 B2
(45) Date of Patent: Oct. 11, 2022

(54) POLYESTER CONTAINING 4-HYDROXYBUTYRATE UNIT

(71) Applicant: MITSUBISHI GAS CHEMICAL COMPANY, INC., Chiyoda-ku (JP)

(72) Inventor: Akira Maehara, Niigata (JP)

(73) Assignee: MITSUBISHI GAS CHEMICAL COMPANY, INC., Chiyoda-ku (JP)

( * ) Notice: Subject to any disclaimer, the term of this patent is extended or adjusted under 35 U.S.C. 154(b) by 0 days.

(21) Appl. No.: 16/642,651

(22) PCT Filed: Aug. 28, 2018

(86) PCT No.: PCT/JP2018/031775
§ 371 (c)(1),
(2) Date: Feb. 27, 2020

(87) PCT Pub. No.: WO2019/044836
PCT Pub. Date: Mar. 7, 2019

(65) Prior Publication Data
US 2020/0255589 A1    Aug. 13, 2020

(30) Foreign Application Priority Data

Aug. 29, 2017  (JP) ............................. JP2017-164468

(51) Int. Cl.
*C08G 63/06* (2006.01)
*C08J 5/18* (2006.01)

(52) U.S. Cl.
CPC ................ *C08G 63/06* (2013.01); *C08J 5/18* (2013.01)

(58) Field of Classification Search
CPC ......... C08G 63/06; C08J 2367/04; C08J 5/18; C08L 101/16; C08L 2201/06; C12P 7/62
See application file for complete search history.

(56) References Cited

U.S. PATENT DOCUMENTS

| | | | | |
|---|---|---|---|---|
| 6,117,658 A * | 9/2000 | Dennis | ................ | C12N 9/0006 435/135 |
| 9,353,258 B2 | 5/2016 | Krishnaswamy et al. | | |
| 2002/0156150 A1* | 10/2002 | Williams | ................ | C12P 7/625 523/113 |
| 2012/0107630 A1* | 5/2012 | Krishnaswamy | ....... | B32B 27/18 428/482 |
| 2013/0065046 A1* | 3/2013 | Krishnaswamy | ....... | C08L 67/04 428/336 |
| 2013/0090449 A1* | 4/2013 | Whitehouse | ....... | C08G 18/6696 528/60 |
| 2013/0225761 A1* | 8/2013 | Whitehouse | ............ | C08L 67/04 524/599 |
| 2014/0030536 A1* | 1/2014 | Krishnaswamy | ......... | B32B 7/12 428/483 |
| 2014/0051787 A1 | 2/2014 | Kann et al. | | |
| 2014/0057326 A1* | 2/2014 | Sato | ..................... | C12N 9/1029 435/135 |
| 2014/0088233 A1* | 3/2014 | Kann | ...................... | C08L 27/06 524/296 |
| 2015/0132512 A1* | 5/2015 | Krishnaswamy | ........ | C08J 3/246 428/35.2 |
| 2015/0203674 A1* | 7/2015 | Weinlein | ................. | C08L 27/06 524/109 |
| 2016/0251494 A1* | 9/2016 | Koyama | ................ | C08K 5/053 524/14 |
| 2016/0326364 A1 | 11/2016 | Minami et al. | | |

FOREIGN PATENT DOCUMENTS

| | | |
|---|---|---|
| JP | 6-181784 A | 7/1994 |
| JP | 7-275344 A | 10/1995 |
| WO | WO 2013/184836 A1 | 12/2013 |
| WO | WO2015/098001 A1 | 3/2017 |

OTHER PUBLICATIONS

Anbreen Anjum et al "Microbial production of polyhydroxyalkanoates (PHAs) and its copolymers: A review of recent advancements", 2016 (Year: 2016).*
Natalia O Zhila et al "Microbial Synthesis and Characterization of Poly (3-Hydroxybutyrate-co4-Hydroxybutyrate) Copolymers", 2011 (Year: 2011).*
H. Mitomo et al "Poly(3-hydroxybutyrate-co-4-hydroxybutyrate) produced byComamonas acidovorans", 2000 (Year: 2000).*
Hori et al Chemical synthesis of high molecular weight poly(3-hydroxybutyrate-co-4-hydroxybutyrate), 1995 (Year: 1995).*
S. Vigneswari et al "Enhanced production of poly(3-hydroxybutyrate-co-4-hydroxybutyrate) copolymer with manipulated variables and its properties", 2009 (Year: 2009).*
Saito et al Microbial Synthesis and Properties of Poly( 3- hyd roxybutyrate-co -4-hyd roxybutyrate), 1996 (Year: 1996).*
Kai-Hee Huong et al. "Biosynthetic enhancement of single-stage Poly(3-hydroxybutyrate-co-4-hydroxybutyrate) production by manipulating the substrate mixtures", J Ind Microbiol Biotechnol (2015) 42:1291-1297 (Year: 2015).*
Extended European Search Report dated May 15, 2020, in Patent Application No. 188501829, citing document AA therein, 6 pages.
International Preliminary Report on Patentability and Written Opinion dated Mar. 3, 2020, in PCT/JP2018/031775, citing documents AA and AL therein, 11 pages.
Anderson, A. J. et al., "Occurrence, Metabolism, Metabolic Role, and Industrial Uses of Bacterial Polyhydroxyalkanoates", Microbiological Reviews, vol. 54, No. 4, 1990, pp. 450-472.

(Continued)

*Primary Examiner* — Frances Tischler
*Assistant Examiner* — Gennadiy Mesh
(74) *Attorney, Agent, or Firm* — Oblon, McClelland, Maier & Neustadt, L.L.P.

(57) ABSTRACT

A medical material comprising film obtained from a polyester wherein the polyester has a weight average molecular weight of 1,250,000 or greater determined by gel permeation chromatography calibrated with polystyrene standards. The polyester comprises a 3-hydroxybutyrate unit and a 4-hydroxybutyrate unit as polymerization units, and proportion of the 4-hydroxybutyrate unit relative to all monomer units is from 14 mol % to 40 mol %. The polyester film is useful for medical apparatus, packaging material for food, plastic sheet for agriculture, flowerpots for seedings, and sheets for construction and engineering.

9 Claims, 7 Drawing Sheets

(56) References Cited

OTHER PUBLICATIONS

Kunioka, M. et al., "Crystalline and Thermal Properties of Bacterial Copolyesters: Poly(3-hydroxybutyrate-co-3hydroxyvaleratea) and Poly(3-hydroxybutyrate-co-4-hydroxybutyrate)", Macromolecules, vol. 22, 1989, pp. 694-697.
Kusaka, S. et al., "Molecular mass of poly[(R)-3-hydroxybutyric acid] produced in a recombinant *Escherichia coli*", Applied Microbiology and Biotechnology, vol. 47, 1997, pp. 140-143.
Valentin, H. E. et al., "Production of poly(3-hydroxybutyrate-co-4-hydroxybutyrate) in recombinant *Escherichia coli* grown on glucose", Journal of Biotechnology, vol. 58, 1997, pp. 33-38.
Yoon, S. C., "Synthesis of Copolymeric PHA by Hydrogenophaga pseudoflava and Ralstonia eutropha H16 from Various Lactones and Their Microstructural Studies", Korean Journal of Applied Microbiology and Biotechnology, vol. 28, No. 2, 2000, pp. 71-79.
Huong, K. H. et al., "Pilot scale production of poly(3-hydroxybutyrate-co-4-hydroxybutyrate) biopolymers with high molecular weight and elastomeric properties", Journal of Bioscience and Bioengineering, vol. 124, No. 1, 2017, pp. 76-83.

\* cited by examiner

RESULT OF MASS SPECTRUM ANALYSIS FOR EACH PEAK
PEAK 1 (METHYL CROTONATE)

PEAK 2 (METHYL 3-HYDROXYBUTANOATE)

PEAK 3 (METHYL 3-METHOXYBUTANOATE)

PEAK 4 (γ-BUTYROLACTONE, GBL)

FIG. 6

PEAK 5 (METHYL 4-METHOXYBUTANOATE)

PEAK 6 (METHYL 4-HYDROXYBUTANOATE)

PEAK 7 (METHYL LEVULINATE, DERIVED FROM FRUCTOSE)

PEAK 8 (METHYL BENZOATE, DERIVED FROM BENZOIC ACID AS INTERNAL STANDARD)

FIG. 7

POLYESTER CONTAINING 4-HYDROXYBUTYRATE UNIT

TECHNICAL FIELD

The present invention relates to a polyester comprising a 3-hydroxybutyrate unit and a 4-hydroxybutyrate unit and having a high molecular weight.

BACKGROUND ART

Many microorganisms accumulate polyhydroxyalkanoates (PHAs) as energy source/carbon source reserve materials in their living system. It is well known that PHAs accumulate when nutrients such as nitrogen, phosphorus, sulfur, oxygen and magnesium are limited while carbon sources are sufficient. PHAs are thermoplastic polyesters that have been drawing attention as a biodegradable and biocompatible plastic, and many studies have been conducted (Non-Patent Document 1). At least 100 types of monomer units constituting PHAs are known, among which a notable example is poly-3-hydroxybutyrate (hereinafter abbreviated as "P(3HB)"), which comprises (R)-3-hydroxybutyrate (hereinafter abbreviated as "3HB"). (Non-Patent Document 1)

P(3HB) has a melting point as high as that of polypropylene (hereinafter abbreviated as "PP") and strength at break also as high as that of PP; however, elongation at break of P(3HB) is 5% or less, which makes it high in crystallinity, hard, yet brittle as a material. In the case where a PHA is industrially used, methods to improve properties include a method to introduce a second component monomer unit for copolymerization and a method to increase molecular weight.

For the methods to introduce a second component monomer for copolymerization, an example is a copolymer (hereinafter abbreviated as "P(3HB-co-4HB)"), in which 4-hydroxybutyrate (hereinafter "4HB") is introduced. (Non-Patent Document 2)

The methods to increase the molecular weight includes a method to introduce a P(3HB) biosynthetic gene (phaCAB) extracted from a P(3HB) synthesizing bacterium *Cupriavidus necator* into Escherichia coli XL 1-Blue, which does not have PHA synthesis system/degradation system, and culture the genetically modified bacterium at pH 6 to produce an ultra high molecular weight P(3HB). (Non-Patent Document 3)

Typically, weight average molecular weight Mw of a wild-type strain P(3HB) that produces P(3HB) is said to be approximately from 500,000 to 1,500,000, approximately from 200,000 to 2,000,000, or approximately from 10,000 to 3,000,000, and it is considered difficult to synthesize an ultra high molecular weight P(3HB) having a Mw of 3,000,000 or greater because a wild-type microorganism has a large number of degrading enzymes in its bacterial cell. Furthermore, because P(3HB) is accumulated in microorganisms as an energy source/carbon source reserve material, upon depletion of the carbon source, P(3HB) is degradated and then used. This phenomenon has been studied for many microorganisms. However, some examples indicate simultaneous occurrence of synthesis and degradation of PHAs. Further, the physiological meaning of the simultaneous occurrence of synthesis and degradation of PHAs is still not clarified. Furthermore, the simultaneous occurrence of synthesis and degradation of PHAs in a PHA-producing wild-type strain is one of the factors that makes the synthesis of the ultra high molecular weight PHA difficult.

A large number of studies on production of P(3HB-co-4HB) has been conducted. To *Cupriavidus necator*, which is a P(3HB)-producing wild-type strain, a carbon source, such as 4-hydroxybutyric acid (4HB), γ-butyrolactone, 1,4-butanediol, 1,6-hexanediol, 1,8-octanediol, 1,10-decanediol and 1,12-dodecanediol, is fed, and after culturing, P(3HB-co-4HB) can be produced.

A method of producing P(3HB-co-4HB) and/or P(4HB) by subjecting *E. coli*, which is a P(3HB)-non-producing bacterium and not a P(3HB)-producing wild-type strain, to genetic modification has been reported. Initially, each of the genes, phaA, phaB, and phaC, respectively of f3-ketothiolase (PhaA), acetoacetyl-CoA reductase (PhaB), and PHA synthase (PhaC), which are derived from *Cupriavidus necator*, that is necessary to produce P(3HB) from acetyl CoA, and additionally genes from succinate degradation pathway in *Clostridium kluyveri* (sucD, 4hbD, orfZ) were introduced to supply 4HB-CoA from succinic acid so as to produce P(3HB-co-4HB) having a molecular weight Mw of approximately 1,800,000 in *E. coli* on glucose as a carbon source; however, the 4HB proportion in the PHA was from 1.3 to 1.5%, which was low. (Non-Patent Document 4)

Furthermore, use of ε-caprolactone or 6-hydroxyhexanoate (or its salt), which is a saponified product of ε-caprolactone, to produce P(3HB-co-4HB) was also reported. In the case where *Cupriavidus necator* was cultured using ε-caprolactone as a carbon source, accumulation of P(3HB-co-4HB) along with the PHA content from 26 to 38% and the 4HB proportion from 30% to 36% was reported (Non-Patent Document 5); however, no molecular weights or mechanical tests were mentioned.

Furthermore, production of P(3HB-co-4HB) with high molecular weight and high elasticity was also reported (Non-Patent Document 6); however, the strength at break was not sufficient.

Furthermore, Patent Document 1 describes an aliphatic polyester resin composition containing a polyhydroxyalkanoate (A), a vinyl acetate-containing copolymer (B), and pentaerythritol (C), where the polyhydroxyalkanoate (A) and the vinyl acetate-containing copolymer (B) are immiscible. The aliphatic polyester resin composition described in Patent Document 1 has an object where, by overcoming slow crystallization, which is a disadvantage of polyhydroxyalkanoates, processability upon molding such as injection molding is improved and the processing speed is enhanced such that blooming in the resulting molded article can be avoided. In Patent Document 1, the objective described above is achieved by blending the vinyl acetate-containing copolymer (B) and the pentaerythritol (C) and allowing the polyhydroxyalkanoate (A) and the vinyl acetate-containing copolymer (B) to be immiscible. In Patent Document 1, conditions required to provide 4HB-containing PHA that can produce a film having a high strength at break and a high elongation at break are not considered.

Patent Document 2 describes medical materials for soft tissue, which are formed from a fiber aggregate and a polyester copolymer of a 3-hydroxybutyrate unit and a 4-hydroxybutyrate unit. Patent Document 2 describes that the 4HB unit content in the 3HB/4HB polyester copolymer is typically from 30 to 99 mol %, preferably from 40 to 98 mol %, and particularly preferably from 60 to 95 mol %. Furthermore, Patent Document 3 describes a method of producing a polyester copolymer comprising from 97 to 80 mol % of 3-hydroxybutyrate unit and from 3 to 20 mol % of the 4-hydroxybutyrate unit in the presence of bacteria of genus *Alcaligenes*. Also, in Patent Documents 2 and 3, conditions required to provide 4HB-containing PHA that can produce a film having a high strength at break and a high elongation at break are not considered.

PRIOR ART DOCUMENTS

Patent Documents

Patent Document 1: WO 2015/098001
Patent Document 2: JP 07-275344 A
Patent Document 3: JP 06-181784 A Non Patent Documents Non-Patent Document 1: Alistair J. Anderson et al., Microbiological Reviews, Vol. 54, No. 4, 450-472, 1990
Non-Patent Document 2: Masao Kunioka et al., Macromolecules, Vol. 22, 694-697, 1989
Non-Patent Document 3: S. Kusaka et al., Applied Microbiology and Biotechnology, Vol. 47, 140-143, 1997
Non-Patent Document 4: Henry E. Valentin et al., Journal of Biotechnology, Vol. 58, 33-38, 1997
Non-Patent Document 5: Sung Chul Yoon et al., Korean Journal of Applied Microbiology and Biotechnology, Vol. 28, No. 2, 71-79, 2000
Non-Patent Document 6: Kai-Hee Huong et al., Journal of Bioscience and Bioengineering, Vol. 124, No. 1, 76-83, 2017

SUMMARY OF INVENTION

Problem to be Solved by the Invention

Physical properties of PHAs are expected to be improved through copolymerization and molecular weight increase of PHAs. P(3HB) has hard and brittle physical properties, and improvement of the physical properties is expected unlikely because the 3-hydroxyvalerate (3HV) unit undergoes cocrystallization even when subjected to copolymerization. However, for a copolymer PHA comprising a second component unit that does not undergo cocrystallization with a 3HB unit, such as a 4HB unit and a 3-hydroxyhexanoate (3HH) unit, significant improvement of physical properties is expected by changing the proportion of the second unit component. In particular, it is known that, P(3HB-co-4HB), in which 4HB units having no side chains compared to 3HB units are copolymerized, undergoes enzymatic degradation by lipases as well as PHA degrading enzyme while PHA comprising 3HB units having side chains or other 3-hydroxyalkanoates does not show degradability by lipases, and the P(3HB-co-4HB) is expected to enhance degradability in a living system and its use as a medical material is expected. However, among production methods that use PHA-producing wild-type strains using 1,4-butanediol, γ-butyrolactone, or 4HB, which have been commonly used as 4HB unit precursors, a method for obtaining a P(3HB-co-4HB) copolymer having a 4HB proportion from 14 mol % to 40 mol % and a weight average molecular weight Mw of 1250000 or greater is not known. Production of P(4HB) having a weight average molecular weight Mw of 2470000 and a number average molecular weight Mn of 480000 has been reported for the cases where genetically modified bacteria (*Delftia acidovorans*) are used. There is a report of production of P(3HB-co-4HB) having a molecular weight of 1800000 with genetically modified *E. coli*; however, the 4HB proportion is only from 1.3 to 1.5%.

As described above, a method for producing a P(3HB-co-4HB) copolymer having, for example, a 4HB proportion from 14 mol % to 40 mol % and a weight average molecular weight Mw of 1250000 or greater, which is expected to significantly enhance the physical properties, is not known.

Since a PHA-producing wild-type strain degrades and uses an accumulated PHA as needed and has a PHA degrading enzyme in its cell, synthesis of an ultra high molecular weight PHA is said to be difficult, and gradual decrease in a molecular weight of PHA during a culture period is understood as a typical phenomenon.

In the case where a PHA is used as a medical material, high purifying technologies, such as endotoxin removal, are employed. Typically, PHA tends to degrade and the molecular weight tends to decrease, as the high purification is performed. Furthermore, in the case where the molecular weight of the PHA after the purification or productization needs to be a high molecular weight, the PHA is required to have an adequately high molecular weight in the stage of culture before purification because the molecular weight decreases by application of heat treatment, such as heating and melting. Even for products for general industries and not as medical materials, purification of a certain degree is necessary, and even higher molecular weights have been demanded for enhancement of physical properties of PHAs after purification. Therefore, a method that can provide a high molecular weight PHA compared to known technologies during culture has been demanded.

An object of the present invention is to provide a high molecular weight 4HB-containing PHA having a high strength at break and a high elongation at break.

Means for Solving the Problem

As a result of diligent research to solve the problems described above, the inventors of the present invention found that P(3HB-co-4HB) having various molecular weights can be obtained even by PHA-producing wild-type strains that have not undergone genetic modification, and excellent physical properties are exhibited by, in particular, P(3HB-co-4HB) which has a weight average molecular weight of 1,250,000 or greater and in which a proportion of a 4-hydroxybutyrate unit is from 14 mol % to 40 mol % relative to all monomer units. The present invention was completed based on the findings described above.

That is, according to the present invention, the following inventions are provided:

(1) A polyester having a weight average molecular weight of 1,250,000 or greater determined by gel permeation chromatography calibrated with polystyrene standards, wherein the polyester comprises at least a 3-hydroxybutyrate unit and a 4-hydroxybutyrate unit as polymerization units, and a proportion of the 4-hydroxybutyrate unit relative to all monomer units is from 14 mol % to 40 mol %.

(2) The polyester according to (1), wherein the polyester has the weight average molecular weight of 1,380,000 or greater determined by gel permeation chromatography calibrated with polystyrene standards.

(3) The polyester according to (1) or (2), wherein the polyester has the weight average molecular weight of 1,800, 000 or greater determined by gel permeation chromatography calibrated with polystyrene standards.

(4) The polyester according to any one of (1) to (3), wherein the polyester has a number average molecular weight of 300,000 or greater determined by gel permeation chromatography calibrated with polystyrene standards.

(5) The polyester according to any one of (1) to (4), wherein the polymerization units consist of the 3-hydroxybutyrate unit and the 4-hydroxybutyrate unit.

(6) The polyester according to any one of (1) to (5), wherein the polyester is a random polymer.

(7) A film containing the polyester according to any one of (1) to (6).

Advantageous Effects of Invention

The P(3HB-co-4HB) having a weight average molecular weight of 1,250,000 or greater, in which a proportion of a 4-hydroxybutyrate unit is from 14 mol % to 40 mol % relative to all monomer units, provided by the present invention, exhibits excellent physical properties.

EMBODIMENTS FOR CARRYING OUT THE INVENTION

Embodiments according to the present invention are described below.

[Polyester]

The polyester according to the present invention has a weight average molecular weight of 1,250,000 or greater determined by gel permeation chromatography calibrated with polystyrene standards, and contains at least a 3-hydroxybutyrate unit and a 4-hydroxybutyrate unit as polymerization units, and a proportion of the 4-hydroxybutyrate unit relative to all monomer units is from 14 mol % to 40 mol %.

As described above, one of the characteristics of the polyester according to the present invention is the high molecular weight of 1250000 or greater, which is a weight average molecular weight (Mw) determined by gel permeation chromatography calibrated with polystyrene standards. The weight average molecular weight determined by gel permeation chromatography calibrated with polystyrene standards, is preferably 1,380,000 or greater, more preferably 1,800,000 or greater, and even more preferably 1,900,000 or greater. The weight average molecular weight determined by gel permeation chromatography calibrated with polystyrene standards, may be 2,000,000 or greater, 2,100,000 or greater, 2,200,000 or greater, 2,300,000 or greater, 2,400,000 or greater, 2,500,000 or greater, 2,600,000 or greater, 2,700,000 or greater, 2,800,000 or greater, 2,900,000 or greater, 3,000,000 or greater, 3,100,000 or greater, 3,200,000 or greater, 3,300,000 or greater, 3,400,000 or greater, 3,500,000 or greater, 3,600,000 or greater, 3,700,000 or greater, 3,800,000 or greater, 3,900,000 or greater, or 4,000,000 or greater. The upper limit of the weight average molecular weight determined by gel permeation chromatography calibrated with polystyrene standards, is not particularly limited and is typically 20,000,000 or less, 10,000,000 or less, 8,000,000 or less, 7,000,000 or less, 6,000,000 or less, or 5,000,000 or less. By setting the weight average molecular weight of the polyester to be 1,250,000 or greater, a film having a high strength at break can be produced.

P(3HB-co-4HB) is known as being extensible and flexible; however, in the case where the weight average molecular weight is 1,250,000 or greater, or desirably in the case of an ultra high molecular weight, where the weight average molecular weight is 3000000 or greater, it was found that a strength at break is enhanced while the extensibility is present.

For the polyester according to the present invention, the number average molecular weight (Mn) determined by gel permeation chromatography calibrated with polystyrene standards, is preferably 300,000 or greater. The number average molecular weight determined by gel permeation chromatography calibrated with polystyrene standards, may be 350,000 or greater, 400,000 or greater, 450,000 or greater, 500,000 or greater, 550,000 or greater, 600,000 or greater, 650,000 or greater, 700,000 or greater, 750,000 or greater, 800,000 or greater, 850,000 or greater, 900,000 or greater, 950,000 or greater, or 1,000,000 or greater. The upper limit of the number average molecular weight determined by gel permeation chromatography calibrated with polystyrene standards, is not particularly limited and is typically 10,000,000 or less, and may be 5,000,000 or less, 400 or less, 3,000,000 or less, or 2,000,000 or less.

The ratio of Mw to Mn (Mw/Mn) is not particularly limited and is preferably from 1.0 to 10.0, more preferably 1.0 to 8.0, even more preferably from 1.0 to 7.0, yet even more preferably from 1.0 to 6.0, yet even more preferably from 1.0 to 5.0, and yet even more preferably from 1.0 to 4.0.

The measurement of the weight average molecular weight by gel permeation chromatography calibrated with polystyrene standards, can be performed by the same method described as that described in Examples below.

The polyester according to the present invention contains at least a 3-hydroxybutyrate unit and a 4-hydroxybutyrate unit as polymerization units. That is, the polyester according to the present invention may be a polyester containing a 3-hydroxybutyrate unit and a 4-hydroxybutyrate unit only, as the polymerization units, (that is, the polymerization units consists of the 3-hydroxybutyrate unit and the 4-hydroxybutyrate unit) or may be a polyester containing the 3-hydroxybutyrate unit and the 4-hydroxybutyrate unit as polymerization units and further containing another polymerization unit besides those described above. Examples of such another polymerization unit include lactate (LA), glycolate (GA), 3-hydroxypropionate (3HP), 3-hydroxyvalerate (3HV), 5-hydroxyvalerate (5HV), 5-hydroxyhexanoate (5HH), 6-hydroxyhexanoate (6HH), 3-hydroxyhexanoate (3HH), and hydroxyalkanoate having 7 or more carbons.

In the present invention, the 3-hydroxybutyrate unit and the 4-hydroxybutyrate unit are represented by the following formulas.

3-Hydroxybutyrate unit: —OCH(CH$_3$)CH$_2$C(=O)—

4-Hydroxybutyrate unit: —OCH$_2$CH$_2$CH$_2$C(=O)—

One of the characteristics of the polyester according to the present invention is that the proportion of the 4-hydroxybutyrate unit is from 14 mol % to 40 mol % relative to all monomer units.

The proportion of the 4-hydroxybutyrate unit relative to all monomer units may be 15 mol % or greater, 16 mol % or greater, 17 mol % or greater, 18 mol % or greater, 19 mol % or greater, 20 mol % or greater, 20.2 mol % or greater, 20.6 mol % or greater, 21 mol % or greater, 22 mol % or greater, 23 mol % or greater, 24 mol % or greater, 25 mol % or greater, 26 mol % or greater, 27 mol % or greater, or 28 mol % or greater.

The proportion of the 4-hydroxybutyrate unit relative to all monomer units may be 35 mol % or less, 34 mol % or less, 33 mol % or less, 32 mol % or less, 31 mol % or less, 30 mol % or less, 29.9 mol % or less, 29.8 mol % or less, 29 mol % or less, 28 mol % or less, 27 mol % or less, 26 mol % or less, or 25 mol % or less.

The proportion of the 4-hydroxybutyrate unit relative to all monomer units is preferably 20.2 mol % or greater, 20.6 mol % or greater, 21 mol % or greater, 22 mol % or greater, 23 mol % or greater, 24 mol % or greater, or 25 mol % or greater, but 29.9 mol % or less, 29.8 mol % or less, 29 mol % or less, 28 mol % or less, or 27 mol % or less. An example of the proportion of the 4-hydroxybutyrate unit relative to all monomer units is from 21 mol % to 29 mol %.

In the case where the weight average molecular weight of the polyester is 1250000 or greater, in the range of 14 mol % to 40 mol % for the proportion of the 4-hydroxybutyrate unit relative to all monomer units, the elongation at break of the produced film tends to increase as the proportion of the 4-hydroxybutyrate unit relative to all monomer units is increased. In the present invention, a high strength at break and a high elongation at break can be both achieved in a well-balanced manner by combining the weight average molecular weight of the polyester of 1250000 or greater and the proportion of the 4-hydroxybutyrate unit relative to all monomer units from 14 mol % to 40 mol %.

The proportion of the 4-hydroxybutyrate unit relative to all monomer units can be measured in accordance with the method described in Examples below.

The polyester according to the present invention may be any one of random polymers, block polymers, alternating polymers, or grafted polymers, and is preferably a random polymer.

[Method for Producing Polyester]

The polyester according to the present invention can be produced by culturing microorganisms having P(3HB)-producing capability in the presence of ε-caprolactone (also known as 6-hexanolactone), 6-hydroxyhexanoate which is a saponified product of ε-caprolactone, or its salt as a carbon source.

As the microorganisms having P(3HB)-producing capability, microorganisms of the genera of *Cupriavidus, Alcaligenes, Ralstonia, Delftia, Comamonas, Hydrogenophaga, Burkholderia, Escherichia, Azotobacter, Methylobacterium, Paracoccus, Acinetobacter, Aeromonas, Allochromatium, Azorhizobium, Bacillus, Caulobacter, Chromobacterium, Ectothiorhodospira, Klebsiella, Nocardia, Pseudomonas, Rhodobacter, Rhodococcus, Rhodospirillum, Rickettsia, Sinorhizobium, Sphingomonas, Synechocystis, Thiococcus, Thiocystis, Vibrio,* or *Wautersia* can be used. Among these, genus *Cupriavidus* is preferred, and *Cupriavidus necator* is more preferred. For example, *Cupriavidus necator* $H_{16}$ (ATCC17699) can be used.

Note that, with the *Cupriavidus necator* $H_{16}$ wild-type strain, 3HB, 3HV, 4HB, 5HV or the like can be adequately incorporated into PHA; however, use of genetically modified bacteria, in which a PHA synthase gene having a different substrate specificity has been introduced, enables polymerization of another hydroxy acid into the PHA. Thus, in addition to *Cupriavidus necator* $H_{16}$ strain, its genetically modified strain, and as described above, other *Cupriavidus* species, as well as the genera of *Alcaligenes, Ralstonia, Delftia, Comamonas, Hydrogenophaga, Burkholderia, Escherichia, Azotobacter, Methylobacterium, Paracoccus,* *Acinetobacter, Aeromonas, Allochromatiurn, Azorhizobium, Bacillus, Caulobacter, Chromobacterium, Ectothiorhodospira, Klebsiella, Nocardia, Pseudomonas, Rhodobacter, Rhodococcus, Rhodospirillum, Rickettsia, Sinorhizobium, Sphingomonas, Synechocystis, Thiococcus, Thiocystis, Vibrio,* and *Wautersia,* that is such genera having PHA-polymerizing capability or being imparted with the PHA-polymerizing capability, can be used.

The pH of the culture solution is typically approximately 4 to approximately 10, preferably approximately 5 to approximately 8, and more preferably approximately 5.8 to approximately 7.5.

The culture temperature is typically from 15° C. to 45° C., preferably from 20° C. to 40° C., and more preferably from 25° C. to 38° C.

The culture method may be any one of batch culture, fed-batch culture, or continuous culture.

The medium component is not particularly limited as long as the medium component is a substance that can be assimilated by the microorganisms to be used.

As the carbon source, for example, organic carbon sources, such as methanol, ethanol, butanol, acetic acid, and butyric acid; inorganic carbon sources, such as carbon dioxide; natural materials, such as yeast extract, molasses, peptone, and meat extract; saccharides, such as arabinose, glucose, mannose, fructose, and galactose; sorbitol, mannitol, and inositol can be used.

As the nitrogen source, for example, inorganic nitrogen compounds, such as ammonia, ammonium salts (ammonium chloride, ammonium sulfate, ammonium phosphate), and nitrate; and/or organic nitrogen-containing substances, such as urea, corn steep liquor, casein, peptone, yeast extract, and meat extract can be used.

Examples of the inorganic component include calcium salts, magnesium salts, potassium salts, sodium salts, phosphate, manganese salts, zinc salts, iron salts, copper salts, molybdenum salts, cobalt salts, nickel salts, chromium salts, boron compounds, and iodine compounds. More specific examples thereof include monopotassium phosphate, dipotassium phosphate, magnesium phosphate, magnesium sulfate, and sodium chloride.

Examples of other organic nutrient source include amino acids, such as glycine, alanine, serine, threonine, and proline; and vitamins, such as vitamin B 1, vitamin B12, and vitamin C.

As methods for producing a 4HB-containing PHA, there are a method in which a precursor that can be converted into 4HB-CoA is added to a PHA-producing wild-type strain for culture and a method that introduces a 4HB-CoA-feeding pathway by genetic modification. In the present invention, in the case where a method in which a precursor that can be 4HB-CoA is added to a PHA-producing wild-type strain for culture is employed, it is preferred to use ε-caprolactone or 6-hydroxyhexanoate or its salts (such as sodium 6-hydroxyhexanoate and potassium 6-hydroxyhexanoate), instead of commonly known 4HB, γ-butyrolactone, or diols having even-numbered and greater or equal to 4 carbons.

For 3HB-CoA, two acetyl CoAs are converted by β-ketothiolase (PhaA) to acetoacetyl-CoA, then further converted by acetoacetyl-CoA reductase (PhaB) to 3HB-CoA. 3HB-CoA is polymerized by PHA synthase (PhaC) to yield P(3HB). Many bacteria that synthesize PHAs formed from short-chain units (having from 3 to 5 carbons) have genes phaA, phaB, and phaC corresponding to these three types of enzymes and have capabilities to synthesize a P(3HB) from acetyl CoAs generated from metabolism of carbon sources, such as saccharides, fats, and alcohols. In such bacteria, in the presence of propionic acid, 3HV-CoA is supplied by condensation reduction of acetyl CoA and propionyl CoA, thus 3HB-CoA and 3HV-CoA coexist, and P(3HB-co-3HV) is accumulated. 3HV-CoA is also supplied from valerate (valeric acid) and pentanol and incorporated into the PHA as a 3HV unit.

Furthermore, in the presence of a substance that becomes a 4HB-CoA precursor, such as 4HB itself, γ-butyrolactone, 1,4-butanediol, 1,6-hexanediol, 1,8-octanediol, or 1,10-decanediol, 4HB-CoA is supplied, thus 3HB-CoA and 4HB-CoA coexist, and P(3HB-co-4HB) is accumulated.

With diols having even-numbered and greater or equal to 6 carbons, 4HB-CoA is formed at the same time as the formation of acetyl CoA by a β-oxidation system.

In a typical synthesis of P(3HB-co-4HB) by using, for example, 4HB, γ-butyrolactone, 1,4-butanediol, 1,6-hexanediol, 1,8-octanediol, or 1,10-decanediol (Appl. Microbiol. Biotechnol. (1989), 30, 569-573, and Polymer International Volume 39, Issue 3, pages 169-174, March 1996), not much amount of high molecular weight P(3HB-co-4HB) was obtained, thereby causing troubles to employ this industrially while excellent physical properties are ensured.

When ε-caprolactone is added to the culture, ε-caprolactone is subjected to ring opening to form 6-hydroxyhexanoate (6HH), then CoA is added thereto to form 6HH-CoA. The acetyl CoA is removed by a β-oxidation system, and 4HB-CoA remains and is incorporated into the PHA to become a 4HB unit. 6HH-CoA is less likely to be incorporated into the PHA because of the substrate specificity of the PHA synthase, and P(3HB-co-4HB) is accumulated.

4HB-CoA also produces acetyl CoA when being subjected to β-oxidation.

A reaction, in which a hydroxy group-containing compound is incorporated into an enzyme-S-PHA complex of the PHA synthase during elongation and break off a thioester between the enzyme and the PHA polymer chain, and then the PHA polymer chain transfers from the enzyme to a chain transfer agent to terminate the PHA polymerization, is called a chain transfer reaction in radical polymerization. There is a possibility that since 4HB and diols are hydroxy group-containing compounds, and γ-butyrolactone also undergoes ring-opening to form 4HB, these hydroxy group-containing compounds may act as chain transfer agents during the PHA polymerization and may stop the polymerization of the PHA. In particular, since one or both of the two hydroxy groups at the terminals of diols can involve in the chain transfer, it is believed that the diols in particular tend to terminate the PHA polymerization, making a high molecular weight PHA unlikely to be obtained.

When ε-caprolactone is subjected to ring opening to form 6HH, which is a hydroxy group-containing compound. The 4HB-CoA can be a substrate for the PHA synthase, but the 6HH-CoA is less likely to be a substrate. Similarly, it is conceived that the 6HH is less likely to act as a chain transfer agent compared to the 4HB, and thus a higher molecular weight PHA can be obtained when ε-caprolactone is used.

Substance production by microorganisms include growth-associated production and non-growth-associated production.

In the growth-associated PHA production, PHA is accumulated while the bacterial cell component other than the PHA proliferates. In the growth-associated PHA production, acetyl CoA is used by both the PHA synthesis and the bacterial cell proliferation, and the acetyl CoA is less likely to be surplus. It is presumed that, during the growth-associated PHA production, generation of free hydroxy acid due to degradation of the PHA is suppressed, and thus chain transfer reaction is less likely to occur and the molecular weight becomes relatively high.

In the non-growth associated PHA production, the PHA accumulation occurs and increases the PHA content after the proliferation of the bacterial cell component has been stopped. Since the bacterial cell proliferation has stopped, surplus acetyl CoA is used for the PHA production. During the non-growth associated PHA production, it seems that the component temporarily taken into the form of PHA undergoes re-differentiation, and free hydroxy acid is discharged out of the bacterial cell. It is presumed that, in the case where the nitrogen source is depleted in the later stage of the culture, transition from the growth associated production to the non-growth associated production occurs, chain transfer reactions frequently occur, and the synthesis and the degradation tend to occur at the same time (conditions where the molecular weight easily decreases).

In the present invention, it was found that, in the case where the PHA is accumulated in a growth associated manner, a high molecular weight PHA is predominantly accumulated compared to the case where the PHA is accumulated in a non-growth associated manner under nutrient limitation. That is, in the production of polyester according to the present invention, as opposed to the non-growth associated PHA production due to limited nutrients, where proliferation of the bacterial cells and accumulation of the PHA are separated, the growth associated PHA production, where proliferation of the bacterial cells and accumulation of the PHA occur simultaneously, is preferred.

From the culture solution obtained by culturing in accordance with the method of the present invention, dried bacterial cells can be obtained by separating and collecting the bacterial cells by a typical solid-liquid separation means, such as filtration and centrifugal separation, then washing and drying the bacterial cells. The polyester according to the present invention can be collected by a common method, such a method comprising extracting a produced polyester from the dried bacterial cells with an organic solvent such as chloroform, adding a poor solvent such as hexane into this extracted liquid to precipitate the polyester, and collecting the polyester according to the present invention.

[Film]

According to the present invention, a film containing the polyester according to the present invention described above is further provided.

The method for producing the film according to the present invention is not particularly limited, and the film can be produced by forming a film through a common method, such as a solvent casting method or a melt extrusion molding method.

The strength at break of the film according to the present invention is preferably 18 $N/mm^2$ or greater, or may be 19 $N/mm^2$ or greater, 20 $N/mm^2$ or greater, 21 $N/mm^2$ or greater, 22 $N/mm^2$ or greater, 23 $N/mm^2$ or greater, 24 $N/mm^2$ or greater, 25 $N/mm^2$ or greater, 26 $N/mm^2$ or greater, 27 $N/mm^2$ or greater, 28 $N/mm^2$ or greater, 29 $N/mm^2$ or greater, or 30 $N/mm^2$ or greater. The upper limit of the strength at break is not particularly limited and is typically 100 $N/mm^2$ or less, or 50 $N/mm^2$ or less.

The strength at break is measured in accordance with ISO 527-1 and JIS K 7161.

The elongation at break of the film according to the present invention is preferably 300% or greater, or may be 400% or greater, 460% or greater, 470% or greater, 480% or greater, 490% or greater, or 500% or greater. The upper limit of the elongation at break is not particularly limited and is typically 1000% or less, or may be 900% or less, 800% or less, or 700% or less.

The elongation at break is measured in accordance with ISO 527-1 and JIS K 7161.

The modulus of elasticity of the film according to the present invention is preferably 240 N/mm² or greater or may be 250 N/mm² or greater, 270 N/mm² or greater, 300 N/mm² or greater, 350 N/mm² or greater, 400 N/mm² or greater, 450 N/mm² or greater, or 500 N/mm² or greater. The upper limit of the modulus of elasticity is not particularly limited and is typically 1000 N/mm² or less or may be 900 N/mm² or less, or 800 N/mm² or less.

The modulus of elasticity is measured in accordance with ISO 527-1 and JIS K 7161.

In the case where the weight average molecular weight of the polyester is 1250000 or greater, the modulus of elasticity tends to be affected by the proportion of the 4-hydroxybutyrate unit relative to all monomer units. That is, in the range from 14 mol % to 40 mol % of the proportion of the 4-hydroxybutyrate unit relative to all monomer units, the modulus of elasticity of the produced film tends to decrease as the proportion of the 4-hydroxybutyrate unit relative to all monomer units is increased.

The film having the physical properties described above can be obtained by forming a film of the polyester provided by the present invention, "the polyester having a weight average molecular weight of 1250000 or greater determined by gel permeation chromatography calibrated with polystyrene standards, and containing at least a 3-hydroxybutyrate unit and a 4-hydroxybutyrate unit as polymerization units, wherein a proportion of the 4-hydroxybutyrate unit relative to all monomer units is from 14 mol % to 40 mol %".

In the case where the film according to the present invention is produced, the film is formed with the polyester provided by the present invention only, without blending with a vinyl acetate-containing copolymer and/or pentaerythritol. That is, the film of an embodiment according to the present invention may be a film containing the polyester provided by the present invention, no vinyl acetate-containing copolymer, and no pentaerythritol.

The film according to the present invention has excellent physical properties described above, is formed from P(3HB-co-4HB) having excellent biodegradability and biocompatibility, and is useful for, for example, medical apparatus, packaging material for food and others, plastic sheet for agriculture, flowerpots for seedings, and sheets for construction and engineering.

The present invention will be described more specifically hereinafter using examples, but the present invention is not limited to the following examples.

EXAMPLES

Production of Polymer (Jar Culture)

Example 1

PHA was produced by using *Cupriavidus necator* $H_{16}$ (ATCC17699).

A medium obtained by adding 14.24 g/L of fructose into a sterilized medium 1 formed from 2.72 g/L of $KH_2PO_4$, 4.26 g/L of $Na_2HPO_4$, 0.3 g/L of $NaHCO_3$, 2 g/L of $(NH_4)_2SO_4$, 0.2 g/L of $MgSO_4.7H_2O$, 0.2 g/L of a yeast extract, and 3.5 mL of a mineral solution described below was subjected to shaking culture in a test tube at 30° C. for 24 hours to obtain a pre-preculture solution.

Mineral solution: dissolved in water are 6 g/L of $FeC_6H_5O_7.xH_2O$, 2 g/L of $ZnSO_4.7H_2O$, 0.1 g/L of $CuSO_4.5H_2O$, 1 g/L of $MnCl_2.4H_2O$, 0.1 g/L of KI, 0.1 g/L of $(NH_4)_6Mo_7O_{24}.4H_2O$, 0.1 g/L of $CoCl_2.6H_2O$, 0.2 g/L of $H_3BO_3$, 5 g/L of NaCl, and 4 g/L of $CaCl_2.2H_2O$.

In an Erlenmeyer flask having a volumetric capacity of 500 mL containing 100 mL of a medium obtained by adding 14.24 g/L of fructose to the aforementioned medium 1 or a medium obtained by adding 8.86 g/L of fructose and 5.38 g/L of ε-caprolactone, 1 mL of the pre-preculture solution was inoculated and cultured at 30° C. and 150 rpm for 48 hours to 96 hours to obtain a mother culture (preculture solution).

In a 3 L jar fermenter, 2 L of a medium was prepared by changing the amount of $(NH_4)_2SO_4$ of the aforementioned medium 1 to be 12.5 g/L. After he medium was sterilized, 100 mL of the mother culture was inoculated into the medium, and then fed-batch process using 42 mass % fructose and ε-caprolactone was started aseptically through a sterilizing filter (PTFE 0.2 μm pore). Feed rate and feed ratio of the carbon source can be set appropriately. To prevent termination of the bacterial cell proliferation caused by an excessive amount of residual carbon source that was not used up by the bacterial cells in the culture vessel, the culture was started at a feed rate of 42 mass % fructose of approximately 1 to 2 g/h (0.5 to 1 g/h·L) and at a feed rate of ε-caprolactone of approximately 0.2 to 0.5 g/h (0.1 to 0.25 g/h·L), which were low flow rates, and these feed ratee were increased stepwise or continuously as the bacterial cells proliferated. The ventilation volume was controlled to 0.2 to 0.3 L/min, the agitation speed was controlled to 500 to 700 rpm, the culture temperature was controlled to 36° C., and the lower limit of the culture pH was controlled to 6.0. 12.5% ammonia water was used as a pH-adjusting alkali. The ratio of ε-caprolactone to fructose was approximately 0.5. The culture was terminated at 100 hours after the start of the culture.

After the culture, the bacterial cells were collected by centrifugal separation, frozen at −20° C., and then subjected to lyophilization.

The method of extracting and purifying the PHA from the bacterial cells was performed as described below. In a glass Erlenmeyer flask with a screw cap, approximately 4 to 10 g of the lyophilized bacterial cells were suspended in 400 mL chloroform and subjected to extraction at 30° C. for 24 to 48 hours. The obtained viscous solution was filtered by a filter paper to remove the bacterial cell residue. The obtained clear solution was concentrated to approximately 100 to 200 mL by an evaporator, and the PHA was precipitated by 5-fold amount of hexane, which was a poor solvent. The obtained white precipitates were washed with ethanol and then vacuum-dried to obtain purified PHA.

Example 2

The same procedure as in Example 1 was performed except for changing the culture temperature in the jar culture to 34° C. and changing the culture time to 112.5 hours.

Example 3

The same procedure as in Example 1 was performed except for changing the culture temperature in the jar culture to 30° C., using a medium in which the amount of $(NH_4)_2SO_4$ was changed to 15 g/L, and changing the culture time to 149 hours.

Example 4

The same procedure as in Example 1 was performed except for using a medium in which the amount of $(NH_4)_2SO_4$ in the jar culture was changed to 10 g/L.

Example 5

The same procedure as in Example 1 was performed except for using a medium in which the amount of $(NH_4)_2SO_4$ in the jar culture was changed to 15 g/L and changing the culture time to 184.8 hours.

Example 6

The same procedure as in Example 1 was performed except for setting the ratio of ε-caprolactone to fructose in the jar culture to 0.7 and changing the culture time to 113.5 hours.

Example 7

The same procedure as in Example 1 was performed except for changing the culture time in the jar culture to 112 hours.

Example 8

The same procedure as in Example 1 was performed except for using a medium in which the amount of $(NH_4)_2SO_4$ in the jar culture was changed to 7.5 g/L, using a 4N NaOH solution as the pH-adjusting alkali, and changing the culture time to 122.5 hours.

Example 9

The same procedure as in Example 1 was performed except for changing the culture temperature in the jar culture to 37° C., using a medium in which the amount of $(NH_4)_2SO_4$ was changed to 7.5 g/L, using a 4N NaOH solution as the pH-adjusting alkali, and changing the culture time to 102.5 hours.

Example 10

The same procedure as in Example 1 was performed except for setting the ratio of ε-caprolactone to fructose in the jar culture to 0.4 and changing the culture time to 94.5 hours.

Example 11

The same procedure as in Example 1 was performed except for changing the culture temperature in the jar culture to 37° C.

Example 12

The same procedure as in Example 1 was performed except for changing the culture temperature in the jar culture to 38° C.

Example 13

The same procedure as in Example 1 was performed except for changing the culture temperature in the jar culture to 38° C., using a medium in which the amount of $(NH_4)_2SO_4$ was changed to 7.5 g/L, and changing the culture time to 114.3 hours.

Example 14

The same procedure as in Example 1 was performed except for changing the culture temperature in the jar culture to 38° C., using a medium in which the amount of $(NH_4)_2SO_4$ was changed to 7.5 g/L, using a 4N NaOH solution as the pH-adjusting alkali, and changing the culture time to 114.3 hours.

Example 15

The same procedure as in Example 1 was performed except for using a medium in which the amount of $(NH_4)_2SO_4$ in the jar culture was changed to 7.5 g/L, adding 25 g/L of sodium acetate to the 42 mass % fructose solution, and changing the culture time to 122.5 hours.

Example 16

The same procedure as in Example 1 was performed except for using a medium in which the amount of $(NH_4)_2SO_4$ in the jar culture was changed to 17.5 g/L, using γ-butyrolactone in place of ε-caprolactone, and changing the culture time to 185.8 hours.

Example 17

In an Erlenmeyer flask having the volumetric capacity of 500 mL containing 125 mL of a medium obtained by changing the amount of $(NH_4)_2SO_4$ of the medium 1 to 2.5 g/L, and adding 8.86 g/L of fructose and 5.38 g/L of ε-caprolactone to the medium to which 3 g/L of NaCl was added, 1 mL of the preculture solution in the test tube culture was inoculated and cultured at 30° C. and 150 rpm for 96 hours. Collection of the bacterial cells and the extraction and purification of the PHA were performed in the same manner as in Example 1.

Comparative Example 1

The same procedure as in Example 1 was performed except for changing the culture temperature in the jar culture to 30° C., using a medium in which the amount of $(NH_4)_2SO_4$ was changed to 7.5 g/L, and changing the culture time to 136.5 hours.

Comparative Example 2

The same procedure as in Example 1 was performed except for changing the culture temperature in the jar culture to 36° C., using a medium in which the amount of $(NH_4)_2SO_4$ was changed to 7.5 g/L, using γ-butyrolactone in place of ε-caprolactone, using a 2N NaOH solution as the pH-adjusting alkali, and changing the culture time to 108 hours. The extracted PHA was stored under a dehumidified and deoxygenated condition (RP packaging, available from Mitsubishi Gas Chemical Company, Inc.) at 25° C. for 6 months.

Comparative Example 3

The PHA sample produced by the culture and extraction in Comparative Example 2 was stored in a humidity of 100% at 40° C. for one month.

Comparative Example 4

The PHA sample produced by the culture and extraction in Comparative Example 2 was stored in a humidity of 100% at 25° C. for 6 months.

Comparative Example 5

The PHA sample produced by the culture and extraction in Comparative Example 2 was stored under a dehumidified and deoxygenated condition (RP packaging, available from Mitsubishi Gas Chemical Company, Inc.) at 60° C. for 3 months.

Comparative Example 6

The PHA sample produced by the culture and extraction in Comparative Example 2 was stored under a dehumidified and deoxygenated condition (RP packaging, available from Mitsubishi Gas Chemical Company, Inc.) at 60° C. for 6 months.

Comparative Example 7

The PHA sample produced by the culture and extraction in Comparative Example 2 was stored in a humidity of 100% at 40° C. for 6 months.

Comparative Example 8

The PHA sample produced by the culture and extraction in Comparative Example 2 was stored in a humidity of 100% at 60° C. for one month.

[Analysis of Polymer]
<1H-NMR and 13C-NMR>

Composition analysis and linkage analysis of the purified PHA produced in each of Examples and Comparative Examples was determined using a nuclear magnetic resonance spectrometer (ECA 500, JASCO Corporation). The purified PHA was dissolved in $CDCl_3$ in the concentration of 1.5 mass % and used as a measurement sample. The $^1$H-NMR spectrum was measured at 500 MHz, and $^{13}$C-NMR spectrum was measured at 125 MHz at room temperature.

The 4HB proportion measured by NMR for the PHA in each of Examples or Comparative Examples is shown in Table 3 below.

Figure 1:
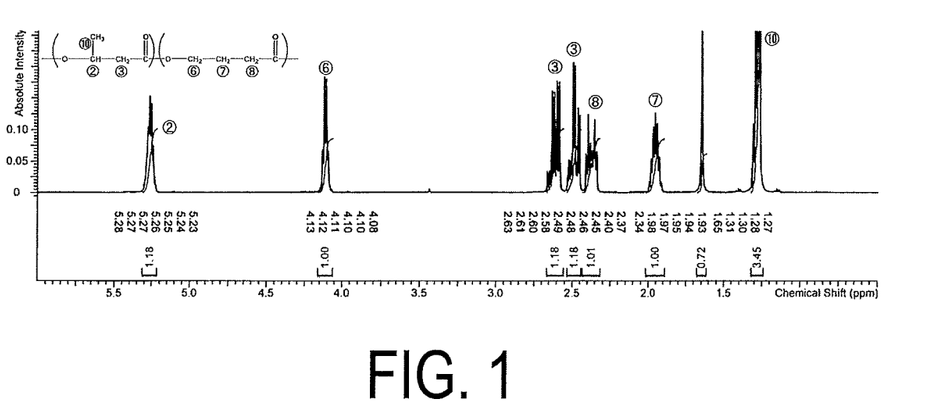
FIG. 1 shows $^1$H-NMR spectrum of PHA of Example 8.
Figure 2:
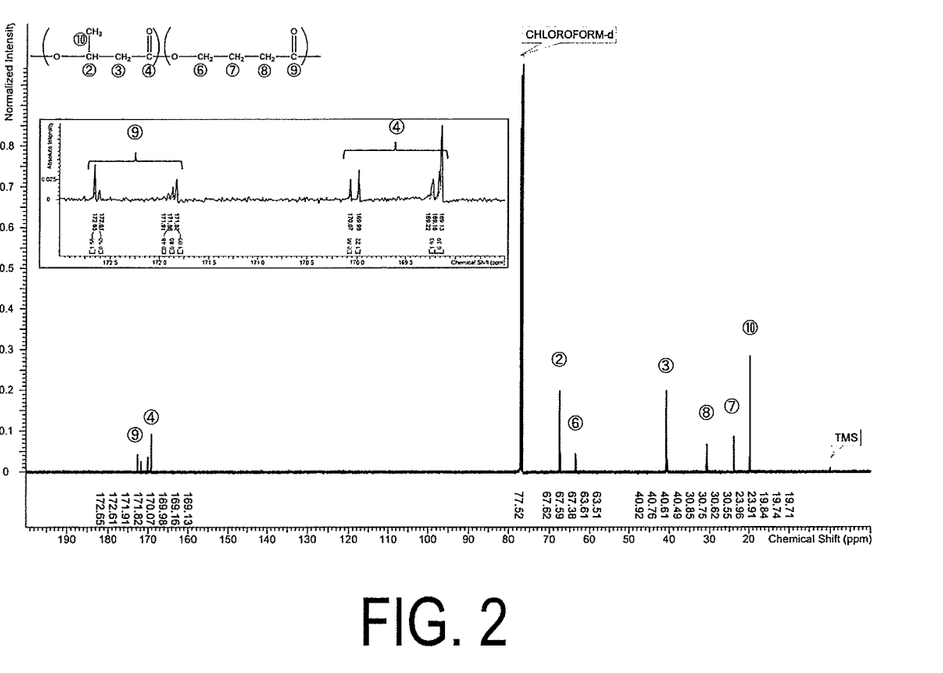
FIG. 2 shows $^{13}$C-NMR spectrum of PHA of Example 8.

The $^1$H-NMR and $^{13}$C-NMR spectra of PHA in Example 8 are shown in FIG. 1 and FIG. 2.

Figure 3:
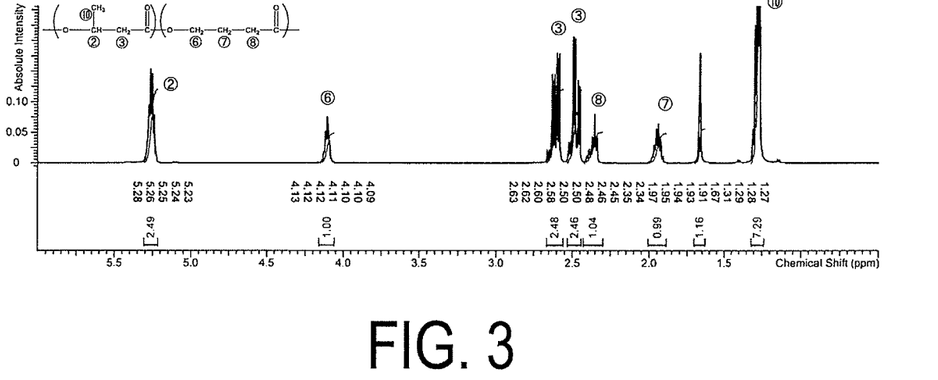
FIG. 3 shows $^1$H-NMR spectrum of PHA of Example 9.
Figure 4:
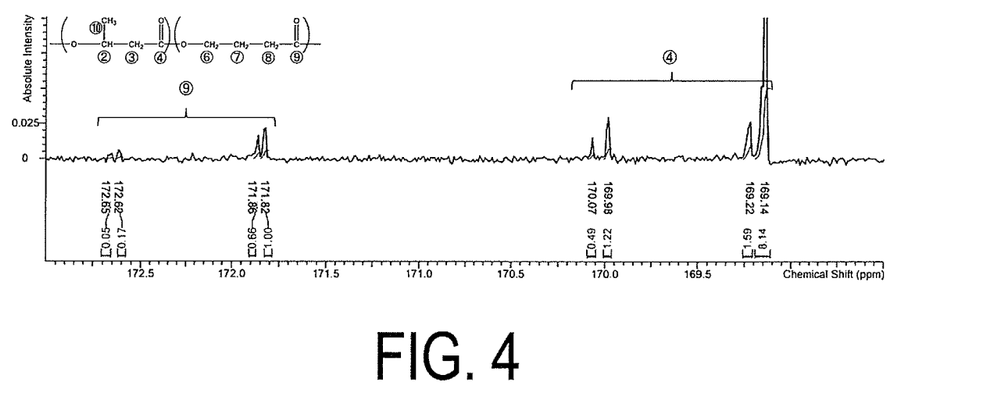
FIG. 4 shows $^{13}$C-NMR spectrum of PHA of Example 9.

The $^1$H-NMR and $^{13}$C-NMR spectra of PHA in Example 9 are shown in FIG. 3 and FIG. 4.

The result of composition analysis of the PHA based on $^1$H-NMR analysis result is shown in Table 1 below.

The result of linkage analysis based on $^{13}$C-NMR analysis result is shown in Table 2 below.

The polymers produced in Examples were random polymers.

TABLE 1

|  | 3HB (5.23-5.41) | 4HB (4.09-4.15) × 0.5 | Total | 3HB mol % | 4HB mol % |
| --- | --- | --- | --- | --- | --- |
| Example 8 | 1.18 | 0.500 | 1.68 | 70.2 | 29.8 |
| Example 9 | 2.49 | 0.500 | 2.99 | 83.3 | 16.7 |

TABLE 2

Chemical shift literature value (ppm)/measured value (ppm)/linkage structure/13C-NMR peak area (%)

|  | 169.15 169.12 3-3-3 | 169.25 169.21 4-3-3 | 170.00 169.97 3-3-4 | 170.08 170.06 4-3-4 | 171.85 171.81 | 171.88 171.84 X-4-3 | 171.92 171.89 | 172.62 172.60 3-4-4 | 172.67 172.64 4-4-4 | 4HB mol % |
| --- | --- | --- | --- | --- | --- | --- | --- | --- | --- | --- |
| Example 8 | 43.3 | 13.1 | 8.3 | 6.0 | 6.8 | 5.4 | 3.3 | 3.4 | 10.6 | 29.8 |
| Example 9 | 61.1 | 11.9 | 9.2 | 3.7 | 7.5 | 5.0 | 0.0 | 1.3 | 0.4 | 16.7 |

PHA Composition Analysis (GC Method)

The composition analysis of the PHA contained in the bacterial cell by GC method was performed as described below. Approximately 10 mg of the obtained dried bacterial cells was weighed in a test tube with a screw cap, mixed with 2 mL of chloroform and 2 mL of an internal standard mixed solution of methanol and sulfuric acid (internal standard: benzoic acid 0.5 g/L; sulfuric acid 3.7 mass %), subjected to a heat treatment at 121° C. for 90 minutes, and then cooled to room temperature to subject the PHA to methyl esterification. After the termination of the reaction, 1 mL of pure water was added. Following vigorous agitation and centrifugal separation, an organic solvent layer was obtained. This organic solvent layer was dehydrated by sodium sulfate and then analyzed by gas chromatography to calculate the PHA component content. Conditions for GC are as shown below.

Figure 5:
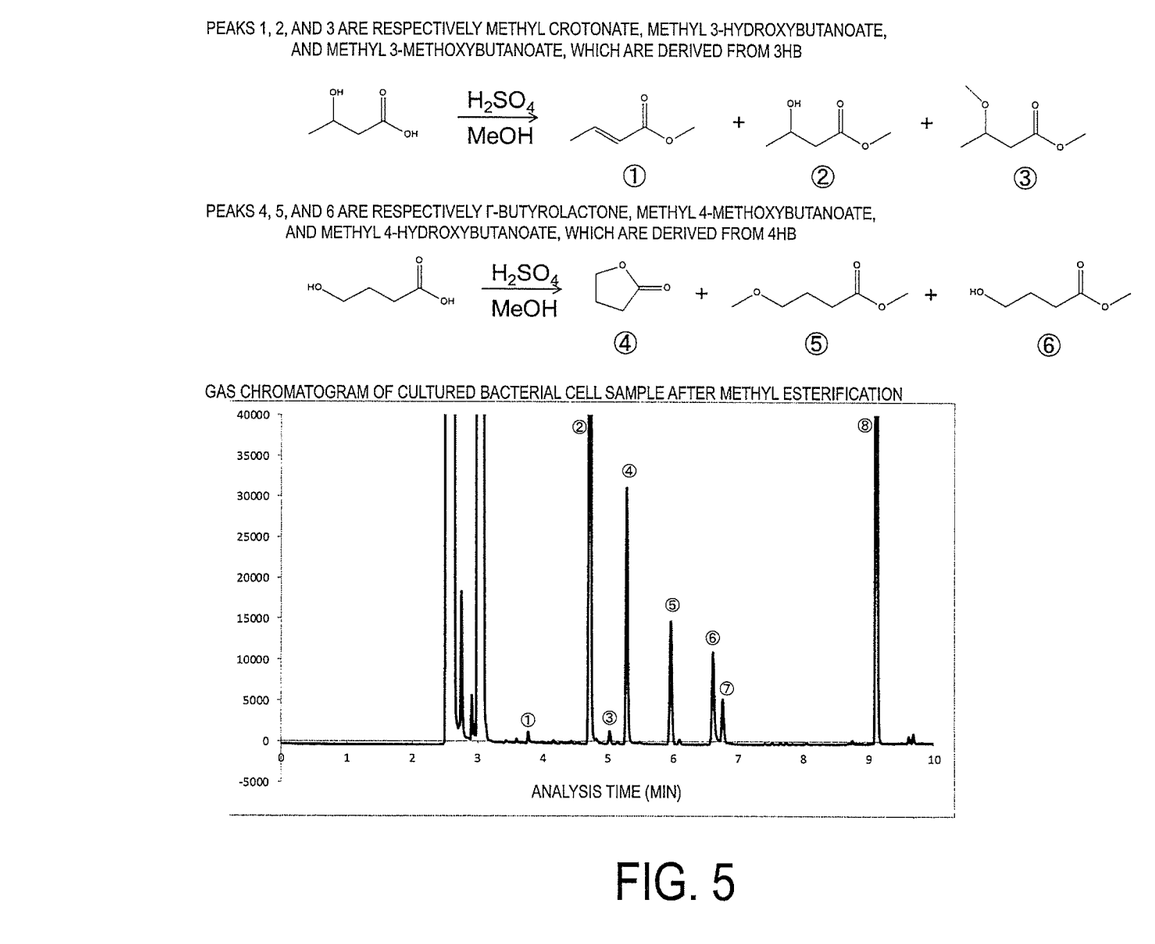
FIG. 5 shows PHA composition analysis (GC-FID chromatogram) of a PHA-containing bacterial cell of Example 8.

Gas Chromatography Analysis Conditions
Instrument: Shimadzu GC-2025
Capillary column: DB-1 (0.25 mm (id)×60 m; film thickness: 1 μm)
Carrier gas: He (3.23 mL/min)
Column temperature: 125° C. 6.5 min—rate 25° C./min-260° C.
Makeup flow rate: 30 mL/min
$H_2$ flow rate: 40 mL/min
Air flow rate: 400 mL/min
Injection: 250° C.
Detector: FID (260° C.)
Split: 1:20
Injection amount: 1 μL
Analysis time: 21.5 min A typical chromatogram of GC-FID (PHA produced in Example 8) is shown in FIG. 5.

Figure 6:
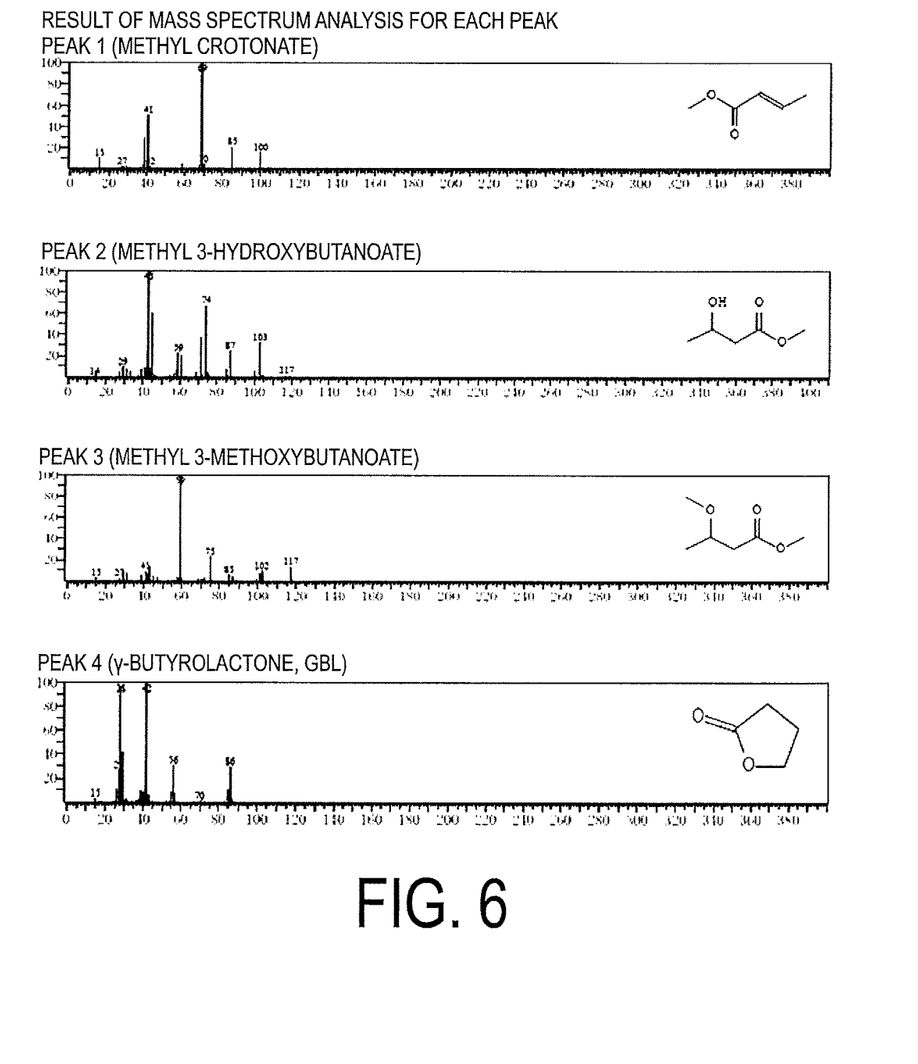
FIG. 6 shows the identification result (GC-MS spectrum) of each of the peaks shown in the chromatogram of FIG. 5.
Figure 7:
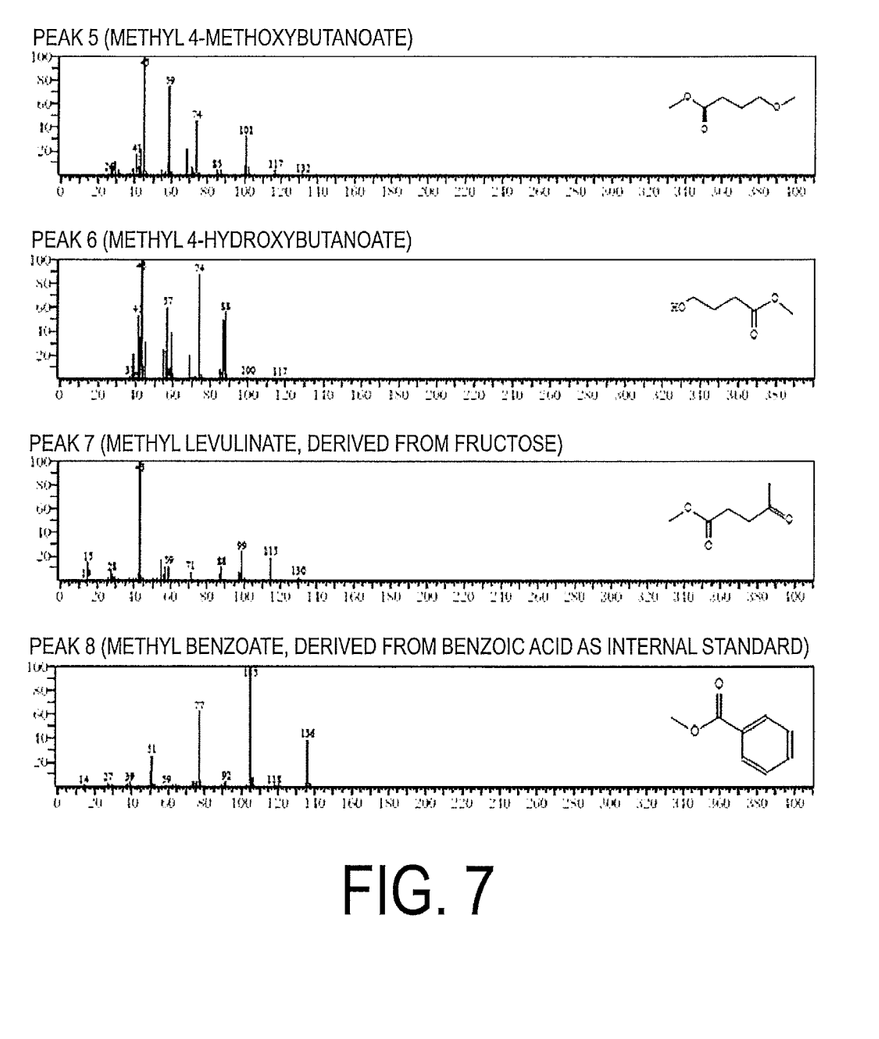
FIG. 7 shows the identification result (GC-MS spectrum) of each of the peaks shown in the chromatogram of FIG. 5.

A plurality of peaks derived from 3HB and 4HB occur in the case where the 4HB-containing PHA or dried bacterial cells containing the PHA was subjected to methyl esterification and then to GC-FID analysis using high resolution capillary columns. Identification of each of the peaks was thus performed by using GC-MS (GCMS-QP2010 Plus, available from Shimadzu Corporation). Conditions for GC were the same as the conditions for GC-FID. The result of identification for each of the peaks is shown in FIG. 6 and FIG. 7.

<PHA Molecular Weight Measurement (Gel Permeation Chromatography (GPC) Method)>

The PHA molecular weight measurement was performed by gel permeation chromatography method as described below. The measurement result of the molecular weight of the PHA in each of Examples or Comparative Examples is shown in Table 3 below.

Chloroform was added to the purified PHA in such an amount that the concentration reaches approximately 0.5 mg/mL, and it was dissolved at 60° C. for 4 hours and then cooled to room temperature. A sample for measurement was obtained after insoluble substances were filtered and removed using a PTFE filter having a pore diameter of 0.2 µm. Conditions for GPC are as shown below.

Instrument: HPLC Prominence system, available from Shimadzu Corporation

Column: Shodex K-806L (two columns in series), available from Showa Denko K.K.

Column temperature: 40° C.

Mobile phase: Chloroform (1 mL/min)

Detector: RI (40° C.)

Standards: Shodex polystyrene molecular weight standards (6870000 to 1270)

Injection amount: 60 µL

Analysis time: 30 minutes

[Production of PHA Film (Solvent Casting Method)]

In 200 mL of chloroform, 5 g of the PHA (PHA in each of Examples or Comparative Examples) was dissolved and poured into an 18×18 cm square-bottom glass container. The chloroform was gradually vaporized to produce a solvent-casted film. A film having a thickness from approximately 0.1 to 0.2 mm was produced. After the vaporization of the chloroform, the film was released from the container and vacuum-dried for 2 weeks or longer, thereafter used in a tensile test.

[Tensile Test Method]

The solvent-casted film was punched out in a shape of JIS K 7127 type 5 to form a dumbbell shape for testing and measured for strength at break, elongation at break, and modulus of elasticity of the film in a condition at a temperature of 23° C. and a test speed of 100 mm/min using AUTOGRAPH AGS-X (available from Shimadzu Corporation). The measurement results are shown in Table 3 below.

TABLE 3

| | 4HB proportion | Molecular weight (×$10^6$) | | | Tensile test of film | | |
| --- | --- | --- | --- | --- | --- | --- | --- |
| | | | | | Strength at break | Elongation at break | Modulus of elasticity |
| | (mol %) | Mw | Mn | Mw/Mn | (N/mm$^2$) | (%) | (N/mm$^2$) |
| Example 1 | 20.2 | 4.21 | 1.14 | 3.7 | 30.4 | 515 | 631 |
| Example 2 | 20.0 | 4.14 | 1.02 | 4.1 | 28.9 | 486 | 631 |
| Example 3 | 16.0 | 4.04 | 0.66 | 6.1 | 31.2 | 410 | 977 |
| Example 4 | 21.2 | 3.86 | 1.04 | 3.7 | 27.4 | 511 | 570 |
| Example 5 | 22.4 | 3.81 | 0.55 | 6.9 | 26.8 | 515 | 511 |
| Example 6 | 22.4 | 3.63 | 0.79 | 4.6 | 27.2 | 507 | 546 |
| Example 7 | 22.7 | 3.25 | 0.54 | 6.0 | 26.7 | 594 | 412 |
| Example 8 | 29.8 | 3.20 | 0.96 | 3.3 | 24.5 | 637 | 297 |
| Example 9 | 16.7 | 3.19 | 0.88 | 3.6 | 31.6 | 473 | 752 |
| Example 10 | 20.1 | 3.12 | 0.44 | 7.0 | 23.0 | 524 | 479 |
| Example 11 | 22.8 | 2.91 | 0.51 | 5.7 | 25.0 | 602 | 371 |
| Example 12 | 24.6 | 2.80 | 0.73 | 3.9 | 21.3 | 587 | 307 |
| Example 13 | 21.3 | 2.64 | 0.39 | 6.8 | 21.1 | 473 | 479 |
| Example 14 | 23.3 | 2.14 | 0.35 | 6.1 | 19.9 | 614 | 244 |
| Example 15 | 21.3 | 2.04 | 0.30 | 6.9 | 21.1 | 544 | 312 |
| Example 16 | 28.2 | 1.96 | 0.49 | 4.0 | 19.7 | 538 | 259 |
| Example 17 | 20.6 | 7.73 | 3.43 | 2.3 | 26.5 | 580 | 360 |
| Comparative Example 1 | 13.2 | 3.06 | 0.68 | 4.5 | 17.3 | 247 | 1156 |
| Comparative Example 2 | 17.9 | 0.75 | 0.32 | 2.3 | 13.0 | 434 | 230 |
| Comparative Example 3 | 17.9 | 0.72 | 0.32 | 2.2 | 11.0 | 429 | 140 |
| Comparative Example 4 | 17.9 | 0.60 | 0.26 | 2.3 | 12.7 | 457 | 205 |
| Comparative Example 5 | 17.9 | 0.49 | 0.18 | 2.7 | 10.2 | 386 | 219 |
| Comparative Example 6 | 17.9 | 0.26 | 0.10 | 2.5 | 6.2 | 211 | 237 |
| Comparative Example 7 | 17.9 | 0.15 | 0.06 | 2.6 | 5.0 | 12 | 242 |
| Comparative Example 8 | 17.9 | 0.14 | 0.05 | 2.6 | 4.8 | 12 | 248 |

[Production of Polymer (Flask Culture)]

Examples 18 to 31

Each PHA was produced by using *Cupriavidus necator* $H_{16}$ (ATCC17699). A medium obtained by adding 14.24 g/L of fructose into a sterilized medium 1 formed from 2.72 g/L of $KH_2PO_4$, 4.26 g/L of $Na_2HPO_4$, 0.3 g/L of $NaHCO_3$, 2 g/L of $(NH_4)_2SO_4$, 0.2 g/L of $MgSO_4.7H_2O$, 0.2 g/L of a yeast extract, and 3.5 mL of the same mineral solution as that in Example 1 was cultured in a test tube at 30° C. for 24 hours to obtain a preculture solution.

In each Erlenmeyer flask having a volumetric capacity of 500 mL containing 100 mL of a medium obtained by adding 8.86 g/L of fructose and 5.38 g/L of E-caprolactone to the medium 1 (Examples 21 to 33; however, the ammonium sulfate concentration was in the amount shown in the table) or a medium obtained by adding 8.86 g/L of fructose and 6.46 g/L of E-caprolactone (Example 34; however, the ammonium sulfate concentration was in the amount shown in the table), 1 mL of the preculture medium was inoculated and cultured at 30° C. and 150 rpm for the period of time shown in the table. The pH before the start of the culture was approximately from 6.8 to 7.5. After the termination of the culture, the bacterial cells were collected by centrifugal separation and lyophilized, and the weight of the dried bacterial cells was measured. Furthermore, the PHA content and the composition determined by GC analysis after the methyl esterification and the measurement result of the molecular weight by gel permeation chromatography (GPC method) are also shown in Table 4 below. The PHA composition analysis by the GC method was performed in the same manner as in Examples 1 to 17 and Comparative Examples 1 to 8.

<PHA Molecular Weight Measurement (GPC Method)>

The measurement of the PHA molecular weight was performed by the gel permeation chromatography method in the same manner as in Examples 1 to 17 and Comparative Examples 1 to 8 except for using the lyophilized bacterial cells in place of the purified PHA.

The invention claimed is:

1. A medical material comprising a polyester having a weight average molecular weight of from 3,000,000 to 8,000,000 determined by gel permeation chromatography calibrated with polystyrene standards, wherein the polyester comprises a 3-hydroxybutyrate unit and a 4-hydroxybutyrate unit as polymerization units, and a proportion of the 4-hydroxybutyrate unit relative to all monomer units is from 16 mol % to 30 mol %,
    wherein, when the medical material is a film, the film has a strength at break of from 23.0 N/mm² to 31.6 N/mm², an elongation at break of from 410% to 637%, and a modulus of elasticity of from 297 N/mm² to 977 N/mm².

2. The medical material of claim 1, wherein the polyester consist of the 3-hydroxybutyrate unit and the 4-hydroxybutyrate unit as the polymerization units.

3. The medical material of claim 1, wherein the polyester is a random polymer.

4. The medical material of claim 1, wherein the medical material is a film.

5. The polyester according to medical material of claim 1, wherein the polyester has a ratio of the weight average molecular weight Mw to a number average molecular weight Mn, (Mw/Mn), is from 1.0 to 10.0.

6. The polyester according to medical material of claim 5, wherein the polyester has the ratio (Mw/Mn) is from 1.0 to 8.0.

7. The to medical material of claim 1, wherein the polyester further comprises at least one polymerization unit selected from the group consisting of lactate (LA), glycolate (GA), 3-hydroxypropionate (3HP), 3-hydroxyvalerate (311V), 5-hydroxyvalerate (5HV), 5-hydroxyhexanoate (5HH), 6-hydroxyhexanoate (6HH), 3-hydroxyhexanoate (3HH), and hydroxyalkanoate having 7 or more carbons.

8. The polyester according to medical material of claim 1, wherein in the polyester the proportion of the 4-hydroxybutyrate unit relative to all monomer units is from 21 mol % to 29 mol %.

9. The medical material of claim 1 wherein the polyester is obtained by culturing an polyhydroxyalkanoate-producing microorganism under a condition where the initial concentration of ammonium sulfite is from 2 g/L to 17 g/L.

* * * * *

TABLE 4

| | Culture Time | Carbon source | | Nitrogen source Ammonium sulfate | Added NaCl | Weight of dried bacterial cells | Bacterial cell component | PHA | 3HB | 4HB | 4HB propor-tion | Molecular weight ×10⁶ | | Mw/Mn |
|---|---|---|---|---|---|---|---|---|---|---|---|---|---|---|
| | | ECL | Fructose | | | | | | | | | | | |
| | H | g/L | g/L | g/L | g/L | g/L | g/L | wt % | wt % | wt % | mol % | Mn | Mw | |
| Example 18 | 96 | 5.38 | 8.86 | 2.0 | | 5.01 | 3.43 | 31.5 | 26.6 | 4.9 | 15.6 | 1.16 | 5.37 | 4.6 |
| Example 19 | 96 | 5.38 | 8.86 | 4.0 | | 5.09 | 3.44 | 32.4 | 27.2 | 5.2 | 16.2 | 1.59 | 5.73 | 3.6 |
| Example 20 | 96 | 5.38 | 8.86 | 7.5 | | 4.93 | 3.32 | 32.7 | 26.7 | 6.0 | 18.4 | 1.93 | 5.69 | 3.0 |
| Example 21 | 96 | 5.38 | 8.86 | 10.0 | | 4.29 | 2.63 | 38.7 | 31.4 | 7.3 | 18.9 | 2.32 | 5.75 | 2.5 |
| Example 22 | 120 | 5.38 | 8.86 | 12.5 | | 4.93 | 2.93 | 40.6 | 30.8 | 9.9 | 24.3 | 2.29 | 5.83 | 2.5 |
| Example 23 | 120 | 5.38 | 8.86 | 15.0 | | 3.44 | 2.02 | 41.3 | 31.1 | 10.2 | 24.7 | 3.24 | 6.33 | 2.0 |
| Example 24 | 144 | 5.38 | 8.86 | 17.5 | | 4.37 | 2.64 | 39.6 | 29.6 | 10.0 | 25.2 | 2.22 | 5.46 | 2.5 |
| Example 25 | 96 | 5.38 | 8.86 | 2.0 | 0.0 | 5.21 | 3.12 | 40.2 | 34.0 | 6.2 | 15.4 | 1.33 | 4.38 | 3.3 |
| Example 26 | 96 | 5.38 | 8.86 | 2.0 | 2.5 | 5.04 | 3.14 | 37.6 | 30.5 | 7.0 | 18.7 | 1.78 | 4.85 | 2.7 |
| Example 27 | 96 | 5.38 | 8.86 | 2.0 | 5.0 | 4.05 | 2.53 | 37.4 | 28.9 | 8.5 | 22.6 | 1.61 | 5.33 | 3.3 |
| Example 28 | 96 | 5.38 | 8.86 | 2.0 | 7.5 | 2.63 | 1.69 | 35.8 | 24.8 | 11.0 | 30.8 | 2.80 | 6.06 | 2.2 |
| Example 29 | 144 | 5.38 | 8.86 | 2.0 | 10.0 | 3.90 | 2.31 | 40.9 | 28.6 | 12.3 | 30.1 | 2.42 | 5.69 | 2.3 |
| Example 30 | 96 | 5.38 | 8.86 | 2.0 | | 4.48 | 2.60 | 40.4 | 33.0 | 7.4 | 18.3 | 2.74 | 6.61 | 2.4 |
| Example 31 | 192 | 6.46 | 7.78 | 2.0 | | 3.97 | 2.09 | 47.3 | 34.9 | 12.4 | 26.3 | 3.01 | 6.50 | 2.2 |